US011896780B2

(12) United States Patent
Beeckler et al.

(10) Patent No.: US 11,896,780 B2
(45) Date of Patent: *Feb. 13, 2024

(54) CATHETER WITH ADJUSTABLE DEFLECTION

(71) Applicant: Biosense Webster (Israel) Ltd., Yokneam (IL)

(72) Inventors: Christopher Thomas Beeckler, Brea, CA (US); Rowan Olund Hettel, Pasadena, CA (US)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 186 days.

This patent is subject to a terminal disclaimer.

(21) Appl. No.: 17/145,446

(22) Filed: Jan. 11, 2021

(65) Prior Publication Data

US 2021/0128878 A1 May 6, 2021

Related U.S. Application Data

(62) Division of application No. 14/715,013, filed on May 18, 2015, now Pat. No. 11,033,715.

(51) Int. Cl.
*A61M 25/01* (2006.01)
*A61M 25/00* (2006.01)

(52) U.S. Cl.
CPC .... *A61M 25/0147* (2013.01); *A61M 25/0054* (2013.01); *A61M 25/0136* (2013.01);
(Continued)

(58) Field of Classification Search
CPC ........ A61J 15/0026; A61M 2039/1033; A61M 2039/1077; A61M 2039/1083;
(Continued)

(56) References Cited

U.S. PATENT DOCUMENTS 5,168,864 A 12/1992 Shockey
5,195,968 A 3/1993 Lundquist et al.
(Continued)

FOREIGN PATENT DOCUMENTS

EP 3 095 482 A1 11/2016
EP 1033107 A1 9/2020
(Continued)

OTHER PUBLICATIONS

Chinese Office Action and Search Report dated May 26, 2020 for Application No. 201610329894.8, 8 pages.
(Continued)

*Primary Examiner* — Shefali D Patel
(74) *Attorney, Agent, or Firm* — Lewis Roca Rothgerber Christie LLP

(57) ABSTRACT

A catheter having a catheter shaft that has a more uniform construction throughout a length of the catheter shaft and is able to provide more than one deflection curvature. The catheter shaft includes a flexible outer tubular member, and a less flexible inner tubular member extending through the outer tubular member in a proximal section of the catheter shaft, wherein the inner tubular member is afforded longitudinal movement relative to the outer tubular member. The catheter also includes at least one puller wire extending through the inner tubular member to deflect a distal deflection section of the catheter shaft, wherein the longitudinal movement of the inner tubular member relative to the outer tubular member enables an operator to select and set a deflection curvature of the distal deflection section.

17 Claims, 13 Drawing Sheets

(52) U.S. Cl.
CPC ..... *A61M 25/0141* (2013.01); *A61M 25/0144* (2013.01); *A61M 2025/0004* (2013.01); *A61M 2025/0175* (2013.01)

(58) Field of Classification Search
CPC .. A61M 2039/1088; A61M 2202/0482; A61M 39/12
See application file for complete search history.

(56) References Cited

U.S. PATENT DOCUMENTS

| | | | |
|---|---|---|---|
| 5,199,950 | A | 4/1993 | Schmitt et al. |
| 5,363,882 | A | 11/1994 | Chikama |
| 5,381,782 | A | 1/1995 | DeLaRama et al. |
| 5,487,757 | A | 1/1996 | Truckai et al. |
| 5,545,200 | A | 8/1996 | West et al. |
| 5,662,606 | A | 9/1997 | Cimino et al. |
| 5,664,580 | A | 9/1997 | Erickson et al. |
| 5,676,653 | A | 10/1997 | Taylor et al. |
| 5,715,817 | A | 2/1998 | Stevens-Wright et al. |
| 5,827,278 | A | 10/1998 | Webster, Jr. |
| 5,944,689 | A * | 8/1999 | Houser ............... A61B 18/1492 606/41 |
| 5,951,539 | A | 9/1999 | Nita et al. |
| 6,013,052 | A | 1/2000 | Durman et al. |
| 6,203,507 | B1 | 3/2001 | Wadsworth et al. |
| 6,585,718 | B2 | 7/2003 | Hayzelden et al. |
| 7,591,799 | B2 | 9/2009 | Selkee |
| 7,918,819 | B2 | 4/2011 | Karmarkar et al. |
| 8,617,087 | B2 | 12/2013 | Schultz et al. |
| 8,747,351 | B2 | 6/2014 | Schultz et al. |
| 2003/0187396 | A1 | 10/2003 | Ponzi |
| 2005/0021004 | A1 | 1/2005 | Cully et al. |
| 2006/0142732 | A1 | 6/2006 | Karmarkar et al. |
| 2010/0168827 | A1 * | 7/2010 | Schultz ............. A61M 25/0133 607/116 |
| 2016/0339207 | A1 | 11/2016 | Beeckler et al. |
| 2020/0222667 | A1 | 7/2020 | Tang et al. |

FOREIGN PATENT DOCUMENTS

| | | |
|---|---|---|
| JP | H08-71157 A | 3/1996 |
| JP | 9-503931 A | 4/1997 |
| JP | 2000-229084 A | 8/2000 |
| JP | 2003-144554 A | 5/2003 |
| JP | 2004-216150 A | 8/2004 |
| JP | 2009-511184 A | 3/2009 |
| JP | 2010-167101 A | 8/2010 |
| WO | WO 2004/045672 A2 | 6/2004 |
| WO | WO 2007/134872 A1 | 11/2007 |

OTHER PUBLICATIONS

European Search Report dated Oct. 4, 2016 for Application No. 16169970.7.
European Examination Report dated Nov. 2, 2017 for Application No. 16169970.7.
Japanese Office Action dated Feb. 25, 2020 for Application No. 2016-098617, 3 pages.
Extended European Search Report dated Aug. 24, 2021, for Application No. 21162748.4, 8 pages.
Translation of Notification of Reasons for Refusal for Japanese Patent Application No. 2016-098617, dated Feb. 25, 2020, 3 pages.
Translation of Notification of Reasons for Refusal for Japanese Patent Application No. 2021-007090, dated Oct. 5, 2021, 4 pages.
Translation of Supplementary Search Report for Chinese Patent Application No. 201610329894.8, dated Feb. 9, 2021, 2 pages.
Translation of First Office Action for Chinese Patent Application No. 2016103298948, dated May 26, 2020, 5 pages.
Translation of Search Report for Chinese Patent Application No. 201610329894.8, dated May 18, 2020, 3 pages.

* cited by examiner

CATHETER WITH ADJUSTABLE DEFLECTION

This application is a divisional of U.S. patent application Ser. No. 14/715,013, entitled "Catheter with Adjustable Deflection," filed May 18, 2015.

FIELD OF INVENTION

This invention relates to electrophysiologic (EP) catheters, in particular, deflectable EP catheters for mapping and/or ablation in the heart.

BACKGROUND

Electrode catheters have been in common use in medical practice for many years. They are used to stimulate and map electrical activity in the heart and to ablate sites of aberrant electrical activity.

In use, the electrode catheter is inserted into a major vein or artery, e.g., femoral vein, and then guided into the chamber of the heart which is of concern. Within the heart, the ability to control the exact position and orientation of the catheter tip is critical and largely determines how useful the catheter is.

Steerable (or deflectable) catheters are generally well-known. A typical catheter has an elongated catheter body, an intermediate deflection section and a distal tip section. The elongated catheter body extends through the patient's vasculature and the shorter intermediate deflection is steered or deflected to reach target tissue in responsive to a rocker arm on a control handle manipulated by an operator, e.g., an electrophysiologist. The catheter typically employs a single-lumened structure for the catheter body, and a multi-lumened structure for the intermediate deflection section which provides a dedicated lumen for each puller wire in order to facilitate deflection. The catheter is therefore a composite of different constructions and materials and consequently may not have uniform characteristics in flexibility, torsional stiffness, pushability and/or rotational accuracy. Assembling puller wires and their respective compression coils, feeding distal portion of the puller wires through their dedicated lumens, and connecting the two structures all require extensive skilled manual labor. Moreover, inner walls of multi-lumened tubing occupy precious space within a catheter.

Because puller-wire-actuated deflection catheters rely on a junction of different flexibility/rigidity between the catheter body and the deflection section, the shape (including tightness of curvature) depends on the location of the junction in relation to the length of the catheter and/or location of the distal anchors of the puller wires. Accordingly, each of these catheters is designed and manufactured to provide one particular deflection curvature. Thus, depending on the specific heart anatomy of the patient in treatment, an electrophysiologist needs to correctly select a catheter curvature prior to start of the procedure, for example, a catheter with a "J" deflection curvature or a catheter with an "F" deflection curvature, to match the heart anatomy. A smaller heart may require a catheter with a tighter or smaller deflection. A larger heart may require a catheter with a looser or larger deflection.

Accordingly, it is desirable that a catheter have a more uniform construction throughout its entire length so that construction and assembly processes are simplified and the catheter exhibit more uniformity in flexibility, torsional stiffness, pushability and/or rotational accuracy along its entire length. It is also desirable that a catheter be adjustable to offer more than one deflection curvature in its catheter shaft.

SUMMARY OF THE INVENTION

The present invention is directed to a catheter with a catheter shaft that has a more uniform construction throughout its length, including an elongated proximal section and a distal deflection section, and a catheter shaft that can adopt more than one deflection curvature. The catheter shaft includes a flexible outer tubular member, and a less flexible inner tubular member extending through the outer tubular member in the elongated proximal section of the catheter shaft, wherein the inner tubular member is afforded longitudinal movement relative to the outer tubular member. The catheter also includes at least one puller wire extending through the inner tubular member to deflect the distal deflection section of the catheter shaft, wherein longitudinal movement of the inner tubular member relative to the outer tubular member enables an operator to select and set a deflection curvature of the distal deflection section.

In some embodiments, the catheter has a catheter shaft with an elongated proximal section and a distal deflection section. The catheter shaft having an outer tubular member with a first center lumen. The catheter also has an inner tubular member having a second center lumen, wherein the inner tubular member extends through the first center lumen of the outer tubular member. The catheter further includes at least one puller wire extending through the second center lumen configured to deflect the distal deflection section In accordance with features of the present invention, the inner tubular member has a lesser flexibility and the outer tubular member has a greater flexibility so as to define a proximal end of the distal deflection section, and the inner tubular member is afforded longitudinal movement relative to the outer tubular member to enable an operator to adjust location of the proximal end along the length of the catheter shaft.

In more detailed embodiments, the outer tubular member has a coil construction, for example, a multi-layered coil construction, wherein each layer of the coil construction has a winding direction different from one or more adjacent layers. For example, an inner layer has a winding in a first direction, a middle layer has a winding in a second direction generally opposite to the first direction, and an outer layer has a winding in the first direction.

In more detailed embodiments, a distal end of the inner tubular member is even for symmetrical bidirectional deflection, or the distal end of the inner tubular member is uneven for asymmetrical bi-directional deflection. The uneven distal end may be sloped, notched or stepped.

In some embodiments, the catheter has a catheter shaft with a flexible multi-layered coil member, and a lumened stiffener member extending through the coil member, wherein a longitudinal position of the stiffener member relative to the coil member is adjustable to set a distal end of the stiffener member in defining a proximal end of the distal deflection section.

In some embodiments, the catheter includes a deflection curvature control handle with a handle body and a piston, wherein the piston is coupled for longitudinal movement with the stiffener member. The piston is adapted to releasably engage the handle body in multiple longitudinal configurations in defining correspondingly multiple locations at which the distal end of the stiffener member can be set.

In some embodiments, the catheter includes a pair of puller wire to provide bi-directional deflection curvatures of the distal section of the catheter shaft. In some embodiments, the distal end of the stiffener member is even to provide symmetrical bi-directional deflection curvatures, or alternatively, the distal end of the stiffener member is uneven to provide asymmetrical bi-directional deflection.

In some embodiments, opposing sections of the coil member along a diameter are fused or fixed together to provide in-plane deflection. For example, portions of adjacent coils along a diameter of the coil member are welded to promote flexion of the coil member in a plane generally perpendicular to the diameter and weld axis.

BRIEF DESCRIPTION OF THE DRAWINGS

These and other features and advantages of the present invention will be better understood by reference to the following detailed description when considered in conjunction with the accompanying drawings wherein.

DETAILED DESCRIPTION OF THE INVENTION

Figure 1:
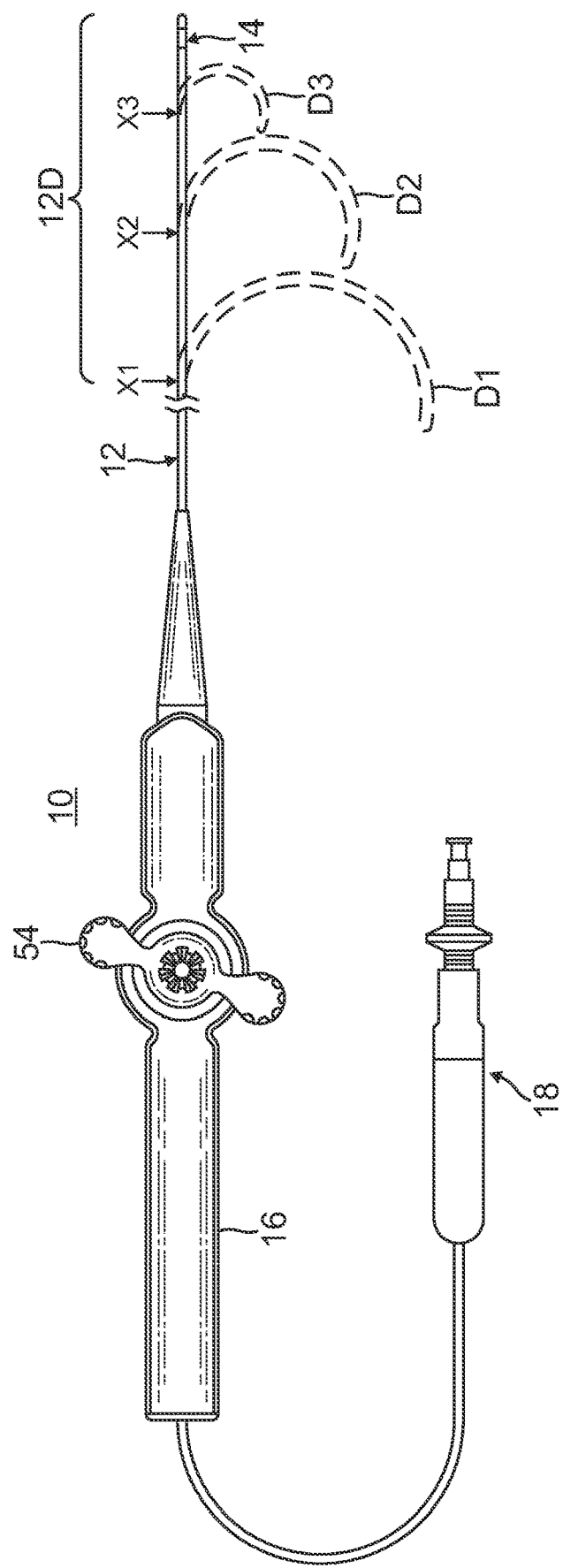
FIG. 1 is a top plan view of a catheter of the present invention, in accordance with some embodiments.

As shown in FIG. 1, a catheter 10 comprises an elongated catheter shaft 12, a distal section 14 with a distal tip electrode 15, a deflection rocker handle 16 attached to the proximal end of the catheter shaft 12 and a deflection curvature adjustment handle 18 proximal of the deflection rocker handle 16. In accordance with a feature of the present invention, the elongated catheter shaft 12 has an adjustable deflection section 12D which allows an operator user to vary and select the deflection curvature, as needed or desired, between multiple deflection curvatures, for example, D1, D2 and D3.

Figure 2A:
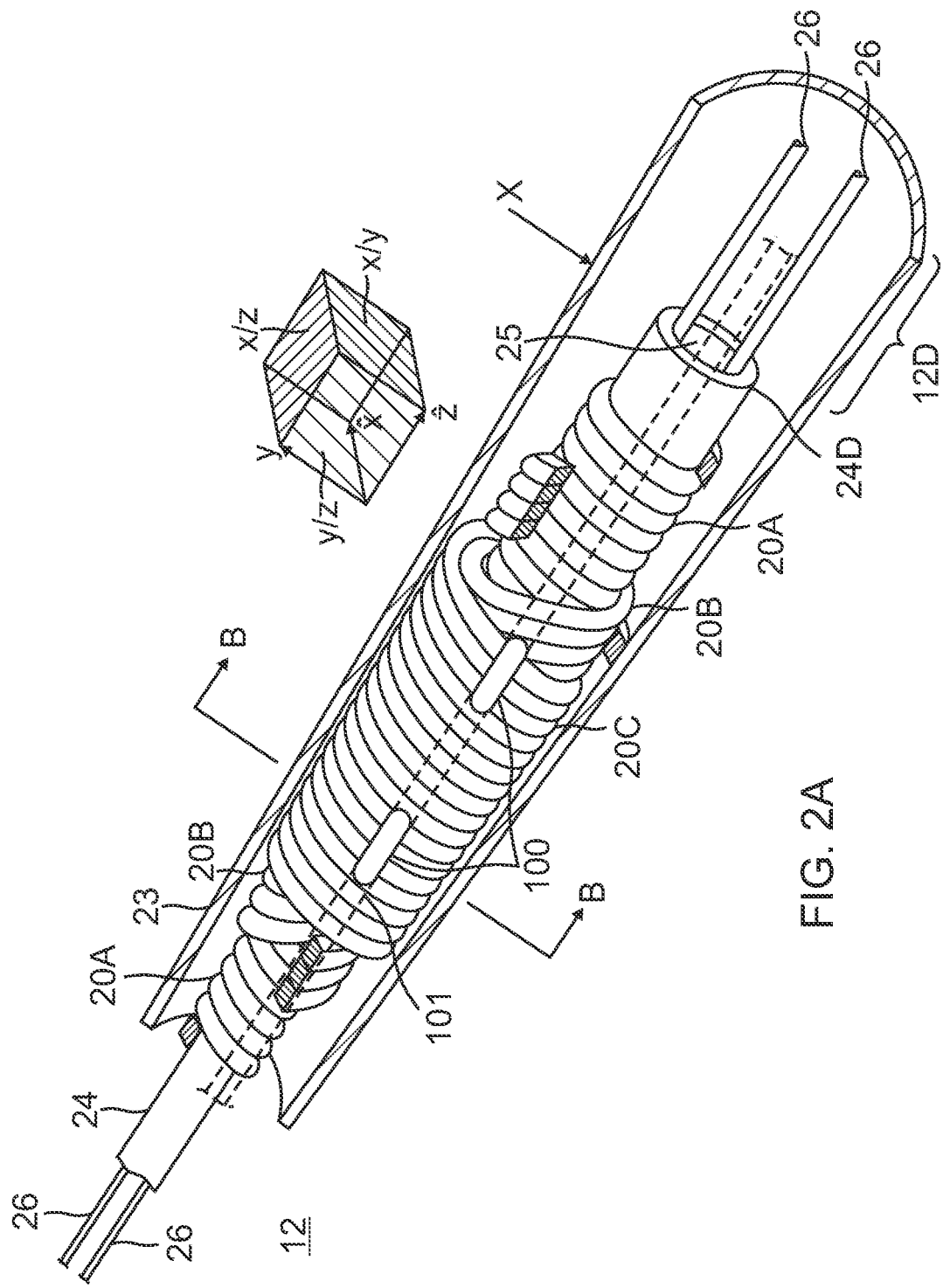
FIG. 2A is a perspective view of the catheter of FIG. 1, including a catheter shaft, with parts broken away.
Figure 2B:
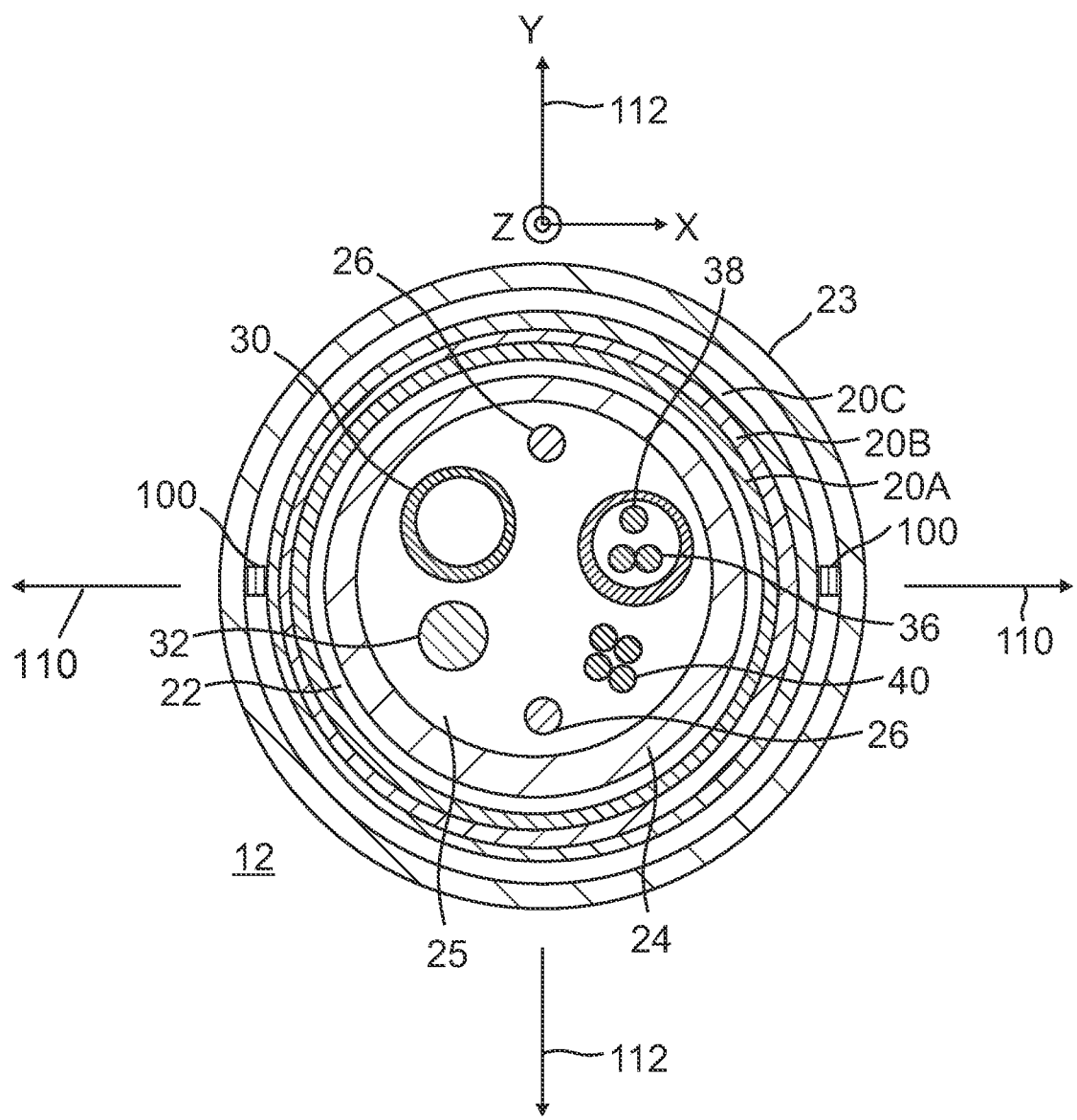
FIG. 2B is an end cross-sectional view of the catheter shaft of FIG. 2A, taken along line B-B.

With reference to FIGS. 2A and 2B, the catheter shaft 12 comprises an elongated tubular construction having a single, axial or central lumen 18. The catheter shaft 12 is flexible, i.e., bendable, but substantially non-compressible along its length. The catheter shaft 12 can be of any suitable construction and made of any suitable material. In some embodiments, the catheter shaft 12 comprises an outer multi-layered coil member 20 to provide flexibility, torsional stiffness, pushability and rotational accuracy so that when the rocker handle 16 is rotated, the catheter shaft 12 and distal section 14 rotates in a corresponding manner.

In some embodiments, the multi-layered coil member 20 includes three layers of compression coils 20A, 20B and 20C, each coil strand or wire having a generally rectangular cross-section, and each coil being wound in a direction different from adjacent layer(s). For example, an inner coil; layer 20A and an outer coil layer 20C have a similar winding direction that is different from a winding direction of a middle layer 20B. In the illustrated embodiment of FIG. 2A, the winding direction of the inner coil layer 20A and the outer layer 20C is to the right of the Y axis and the winding direction of the middle layer 20B is generally opposite to the left of the Y axis. Suitable multi-layered coil members are available from Heraeus Medical Components, LLC and sold under the trademark TRIFLEX. An outer covering or shrink sleeve 23, for example, of any suitable biocompatible plastic such as polyurethane or PEBAX, is provided outside of the outer coil layer 20C to protect and provide a fluid-tight sealed interior of the catheter shaft 12.

The outer diameter of the catheter shaft 12 is not critical, but is preferably no more than about 12 french, more preferably about 7.5 french. The inner diameter of a central lumen 22 defined by the inner coil layer 20A is not critical, but is large enough so that the central lumen can accommodate at least an inner stiffener member 24 that extends through a proximal portion of the catheter shaft 12 and whose distal end 24D defines a proximal end X of the adjustable deflection section 12D of the catheter shaft 12.

The stiffener member 24 is an elongated lumened tubing that is afforded longitudinal movement relative to the multi-layered coil member 20. The stiffener member 24 has sufficient flexibility for maneuverability within a patient's vasculature but also sufficient rigidity to resist compression and deformity along its length within the central lumen 22 of the coil member 20 so to enable deflection of deflection section 12D in response to the one or more puller wires of the catheter 10. The stiffener member 24 has an outer diameter smaller than the inner diameter of the central lumen 22, and an inner diameter that is sufficiently large so that its central lumen 25 can accommodate various components, for example, one or more puller wires, one or more lead wires, irrigation tubing, and any other desired wires, cables or tubes.

To provide more flexibility in a distal portion of multi-layer coil member 20, a lesser number of coils can be used. In the illustrated embodiment of FIG. 3, inner coil layer 20A has a distal end proximal of the distal ends of the middle and outer coil layers 20B and 20C such that the distal portion of 20 has only two coils 20B and 20C instead of three. These distal portions of the coil layers 20B and 20C can be welded to form a tubular end portion 21 to allow for attachment for the puller wire 26 at welds W, as well as to lock the two coil layers together.

Figure 3:
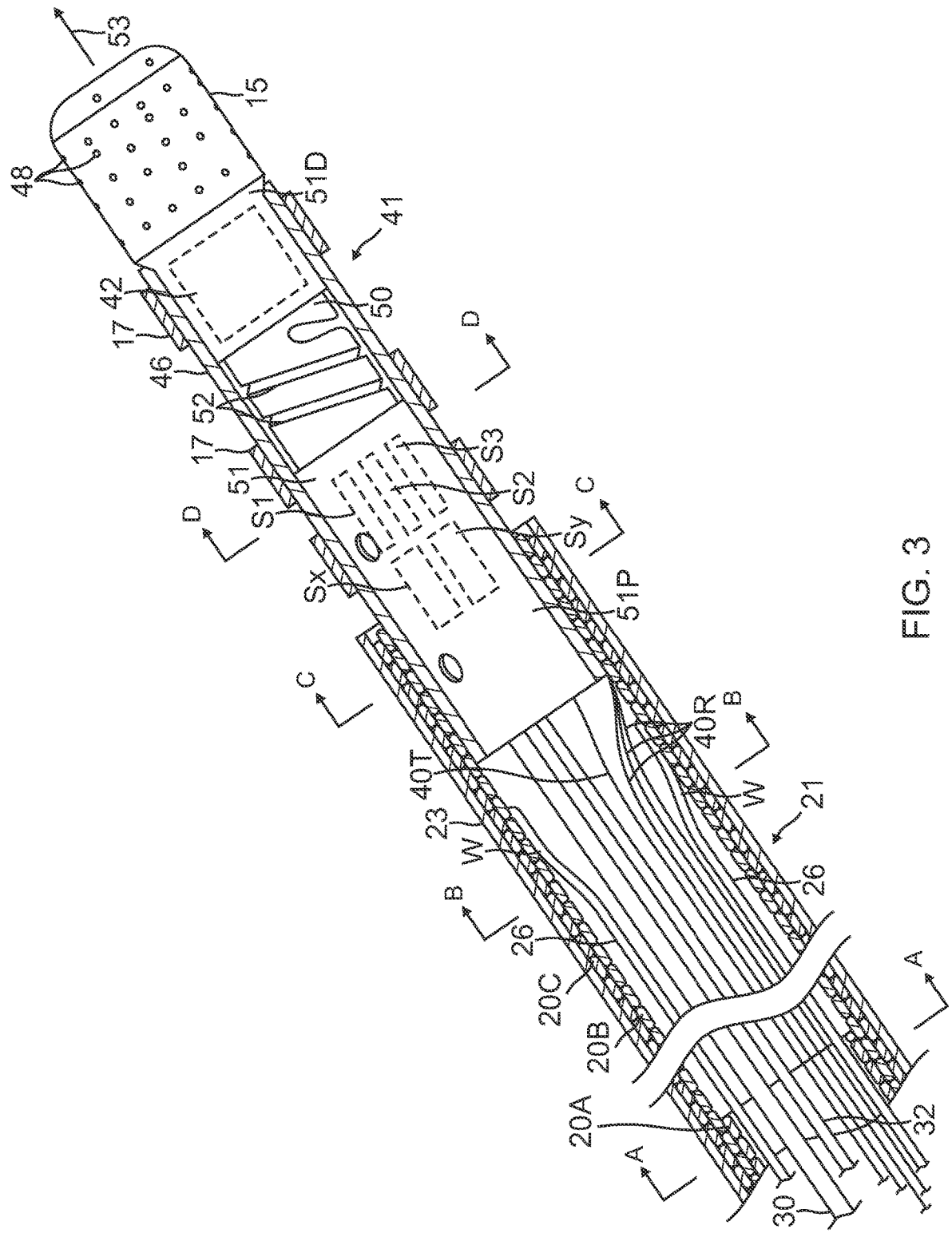
FIG. 3 is a perspective view of the catheter of FIG. 1, including a distal deflection section of the catheter shaft, and a distal tip section, with parts broken away.
Figure 3A:
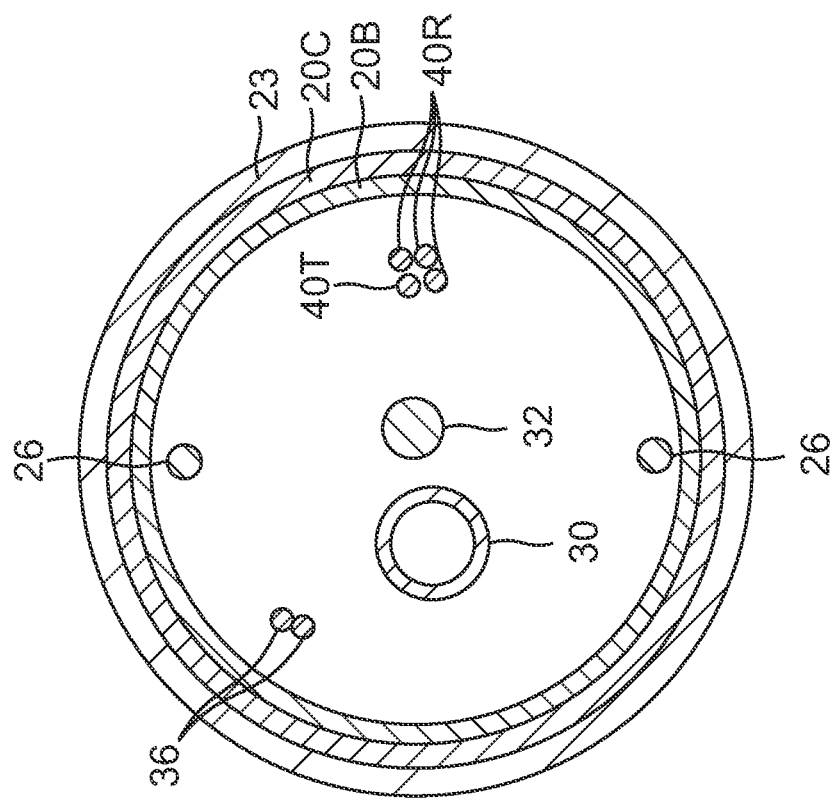
FIG. 3A is an end cross-sectional view of the distal deflection section of FIG. 3, taken along line A-A.
Figure 3B:
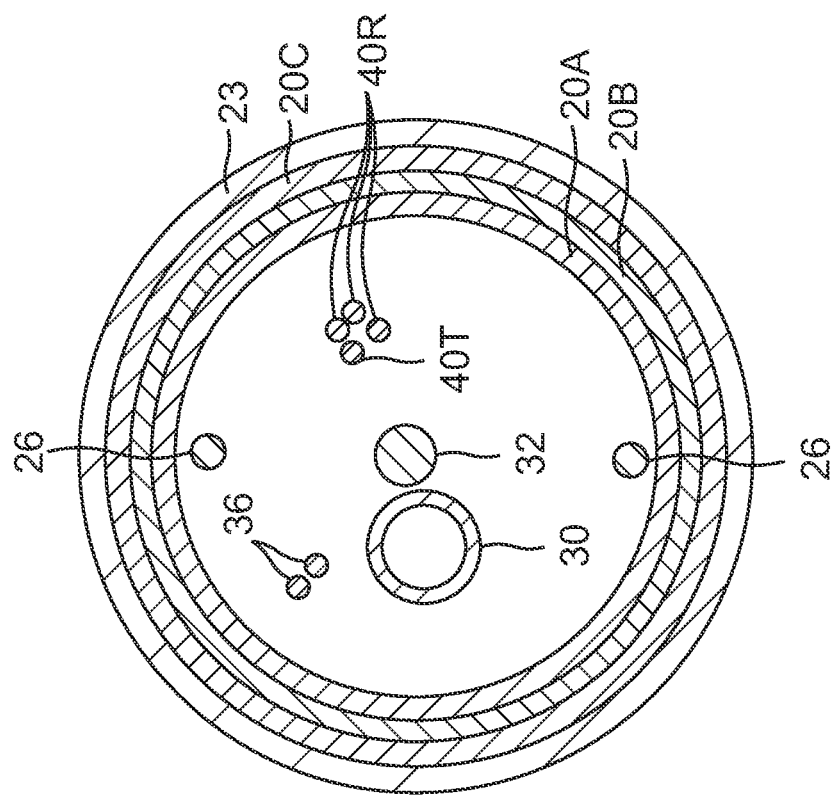
FIG. 3B is an end cross-sectional view of the distal deflection section of FIG. 3, taken along line B-B.

As shown in FIGS. 2B and 3, components extending through the lumen 25 of the stiffener member 24 may include puller wires 26 for bidirectional deflection, lead wire 38 for the distal tip electrode 15, thermocouple wire pair 36, irrigation tubing 30 for delivering irrigation fluid to the distal tip electrode 15, cable 32 for an electromagnetic (EM) force and location sensor subassembly 41 housed in the distal section 14, and lead wires 40T for tip electrode 15 and 40R ring electrodes 17 of the distal section 14. It is understood that the catheter 10 may include a distal electrode section of any configuration, including, for example, focal tip electrodes, lasso electrode assemblies, balloon or basket shaped electrode assemblies, wherein the electrodes may be used for diagnostic and/or therapeutic purposes, such as mapping and/or ablation.

The useful length of the catheter shaft 12, i.e., that portion that can be inserted into the body, can vary as desired. Preferably the useful length ranges from about 100 cm to about 120 cm. The length of the stiffener member is less, so that the catheter shaft 12 has about 5-15 cm of length distally without the stiffener member inside.

With reference to FIG. 3, the distal section 14 includes a short barrier sleeve 46, the distal tip electrode 15 and the pressure sensing subassembly 41 therebetween. The distal tip electrode 15 is configured with a plurality of irrigation ports 48 which weep out fluid delivered by the irrigation tubing 30 (see FIG. 2B), whose distal end terminates in a chamber in the tip electrode. The pressure sensing subassembly 41 includes a resilient member 50 which elastically deforms in response to a force acting on the tip electrode 15, an internal field generator 42 and three electromagnetic sensing coils S1, S2, S3 responsive to the internal field generator 42 which detect deformation of the resilient member 50 in determining the force acting on the tip electrode 15. In the illustrated embodiment, the resilient spring member 50 is a tubular member 51 made of an elastically deformable material, e.g., nitinol. The tubular member 51 has a distal portion 51D, a proximal portion 51P and a mid-portion with a helical slit 52 forming the resilient member 50 which allows longitudinal displacement and angular deflection of the tip electrode 15. Housed in a center lumen of the proximal portion 51P are the electromagnetic sensing coils S1, S2 and S3. The barrier sleeve 46 extends the length of the tubular member, between a distal end of the catheter shaft 12 and the tip electrode 15, to provide a fluid tight seal around the tubular member 51. The barrier sleeve may be constructed of any suitable biocompatible material that is flexible and insulating, including CELCON, TEFLON or heat-resistant polyurethane.

Figure 3D:
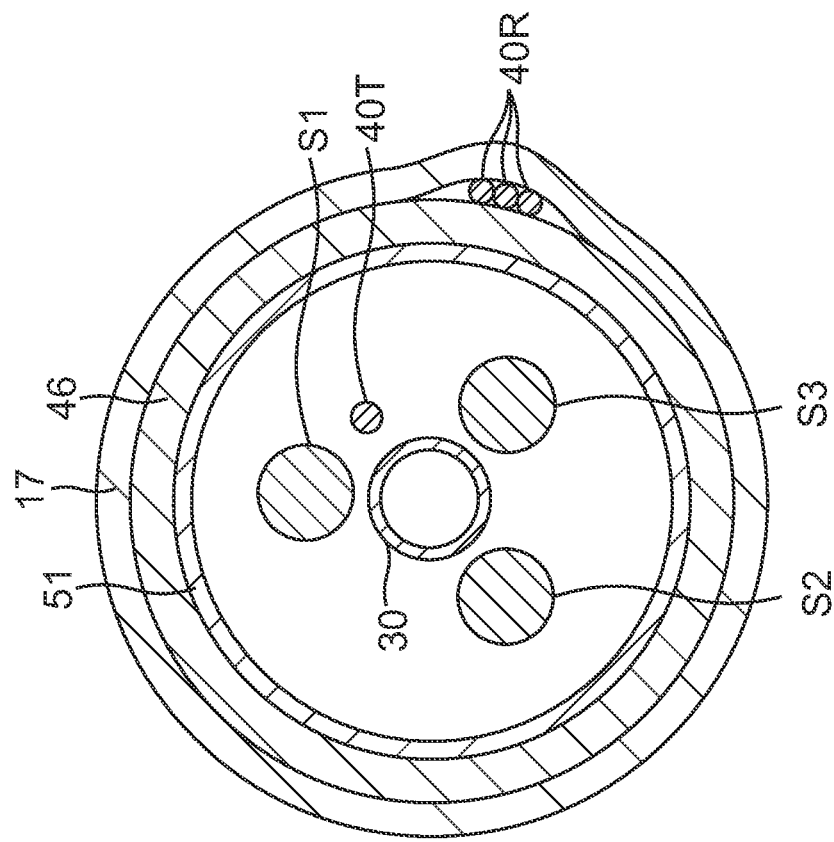
FIG. 3D is an end cross-sectional view of the distal deflection section of FIG. 3, taken along line D-D.

Each of the coils S1, S2 and S3 is generally parallel with the Z or longitudinal axis 53 of the catheter. They are each located at a common longitudinal section in the tubular member 51, but each at different azimuthal angle about the longitudinal axis 53. The coils S1, S2 and S3 are spaced azimuthally 120 degrees apart, at the same radial distance from the longitudinal axis 53. (see FIG. 3D). Longitudinal displacement and/or angular deflection of the distal portion 51D relative to the proximal portion 51P give rise to a differential change in the signal outputs by the coils S1, S2 and S3, depending on the direction and magnitude of deflection, since one or two of these coils move relatively closer to the internal field generator 42. Compressive displacement of the distal portion 51D gives rise to an increase in the signals from each of coils S1, S2 and S3.

Figure 3C:
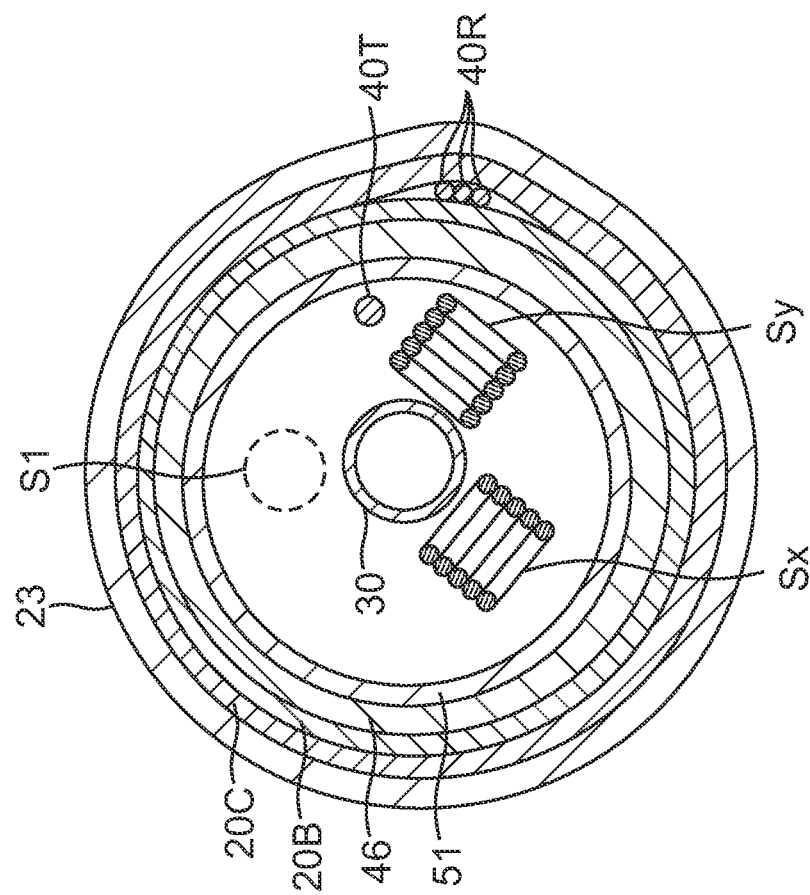
FIG. 3C is an end cross-sectional view of the distal deflection section of FIG. 3, taken along line C-C.

Also housed in the proximal portion 51D, sensors Sx and Sy are responsive to external field generators (not shown) which generate magnetic fields in the vicinity of the patient's body (for example, below the patient's bed) to define an external frame of reference, as shown in the art. The coils Sx and Sy are arranged with generally mutually orthogonal axes with each other and with at least one coil, for example, S1 (see FIG. 3C). Accordingly, the coil Sx is aligned with an X axis and the coil Sy is aligned with a Y axis, and both coils are orthogonal to the coil S1 which is aligned with the Z axis (longitudinal axis 53) with in an (X, Y, Z) coordinate system.

Electromagnetic or magnetic fields are generated by the external field generators Fx, Fy, Fz (not shown) and sensed by the sensor coils Sx, Sy and Sz for detecting position of the catheter. The magnetic fields created by the field generators Fx, Fy and Fz cause the coils Sx, Sy and S1 to generate electrical signals, with amplitudes that are indicative of the position of the distal section 51D relative to the fixed frame of reference of field generators Fx, Fy and Fz. In some embodiments, the three field generators Fx, Fy and Fz generate a magnetic field composed of three differently-oriented field components. Each of these field components is sensed by each sensor coil Sx, Sy and S1, each of which produces a signal composed of three components.

A proximal end of the barrier sleeve 46 and of the proximal portion 51P of the tubular member 51 are received in the welded tubular end portion 21 of the multi-layered coil member 20. Fixedly attached to an inner radial surface of the distal end tubular section 21 is a distal end of each puller wire 26. Accordingly, the distal ends of the puller wires are anchored at or near the distal of the catheter shaft 12, for example, by welds W.

Components including the lead wires 40T and 40R, thermocouple wire pair 36, the irrigation tubing 30 and the sensor cable 32 extend through the welded tubular end portion 21 and into the pressure sensing subassembly 41. The sensor cable 32 includes leads (not shown) to each of the sensors S1, S2, S3, Sx and Sy.

To actuate the puller wires 26, a user manipulates a deflection rocker arm 54 on the control handle 16, as shown in FIG. 1. As known in the art, the rocker arm 54 draws on one or the other puller wire 26 depending on the direction of rotation which deflects the distal section 12D of the catheter shaft in that direction. In accordance with a feature of the present invention, the type or degree of deflection curvature of the catheter 10 as set by a longitudinal position of the stiffener member 24 relative to the catheter shaft 12, and in particular the multi-layer coil member 20, is adjustable by an operator via the deflection curvature adjustment handle 18.

Figure 4:
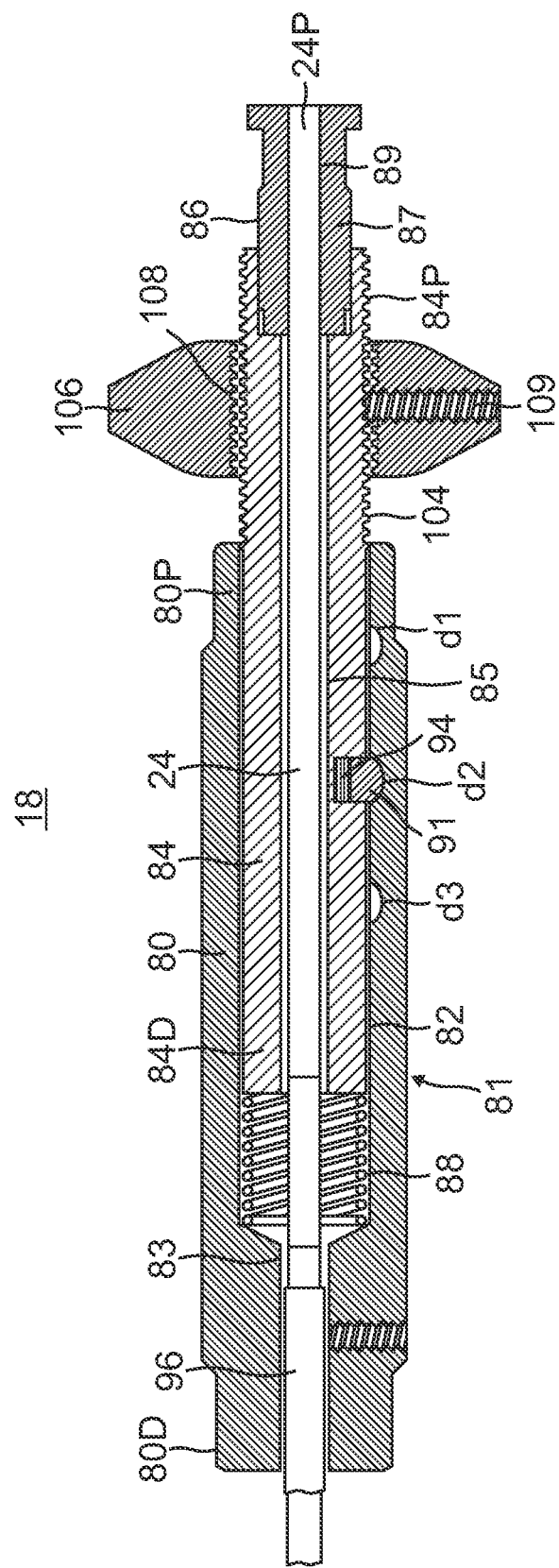
FIG. 4 is a side cross-sectional view of a deflection curvature adjustment handle of FIG. 1.

In the illustrated embodiment of FIG. 4, the deflection curvature adjustment handle 18 comprises a generally cylindrical outer body 80 housing a piston assembly 81. The body 80 has proximal end 80P and distal end 80D. The piston assembly 81 includes a piston 84, a longitudinal piston chamber 82 extending partially therethrough, and a stiffener passage 83 extending partially therethrough. The piston chamber 82 extends from the proximal end 80P of the outer body 80 partway into the handle 18, but does not extend out the distal end 80D of the outer body. The stiffener passage 83, which has a diameter less than that of the piston chamber 82, extends from the distal end of the piston chamber to the distal end 80D of the outer body 80.

The piston 84, having proximal end 84P and distal end 84D, is slidably mounted within the piston chamber 82. A proximal fitting 86 is mounted in and fixedly attached to the proximal end 84P of the piston 84. The proximal fitting 86 includes a tubular distal region 87 that extends distally from the main body of the proximal fitting and into the proximal end 84P of the piston. The piston 84 has a longitudinal axial passage 85 which is coaxial and connects with an axial passage 89 formed in the proximal fitting 86. The stiffener member 24 has a proximal end 24P that is fixed, e.g., by adhesive, to the proximal fitting 86 and thus coupled to the piston so that movement of the piston results in movement of the stiffener member 24. The stiffener member 24 extends through the axial passages 85 and 89 and out the distal end of the deflection curvature adjustment handle 18.

Figure 5A:
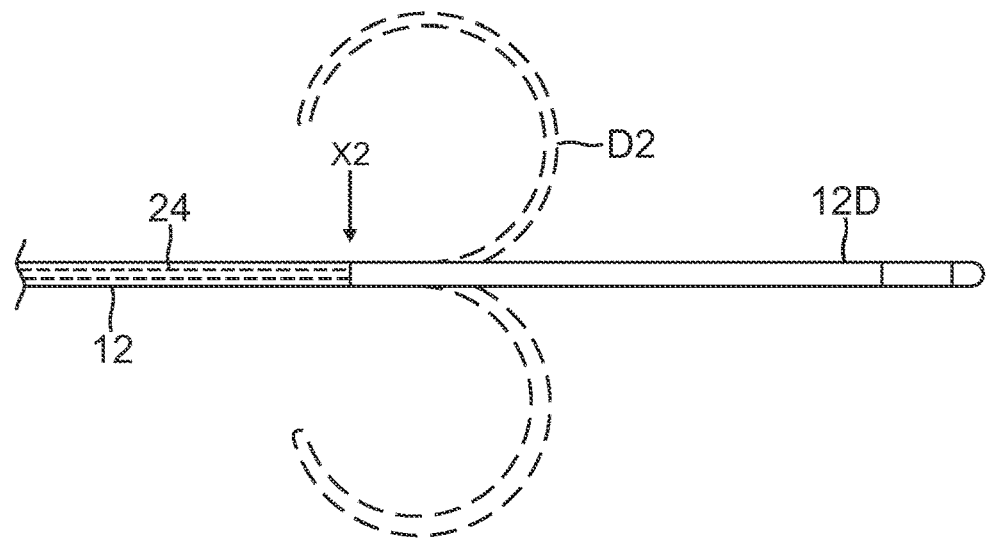
FIGS. 5A, 5B and 5C are schematic representations of symmetrical bi-directional deflection curvatures of different types or tightness provided by the catheter shaft of FIG. 1.
Figure 5B:
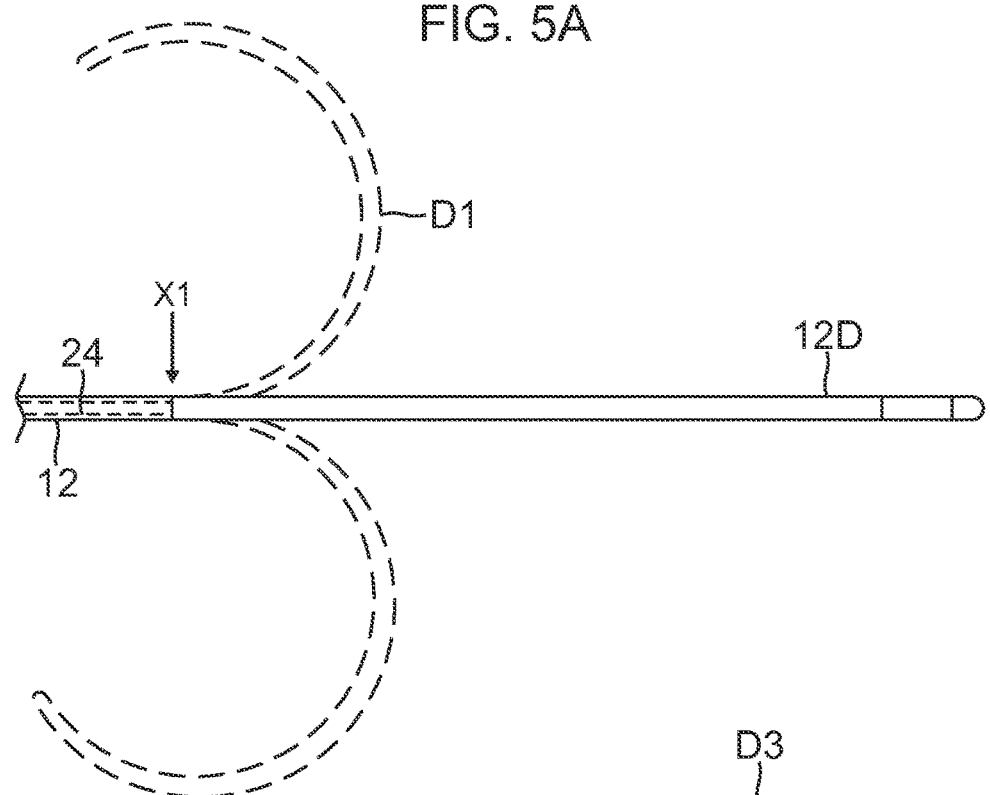
Figure 5C:
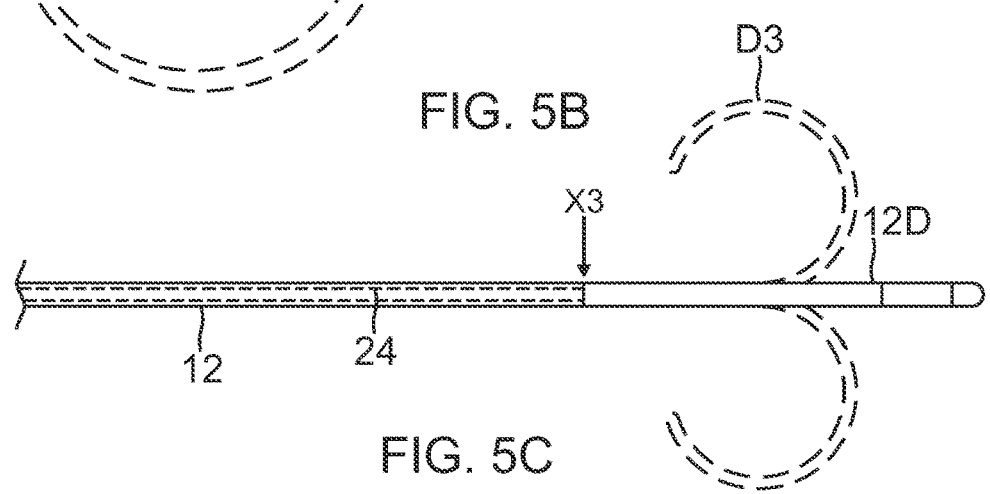

To guide an operator in selecting predetermined types or degrees of deflection curvature of the catheter, the adjustment handle 18 is configured for longitudinal movement of the piston 84 relative to the cylindrical body 80 in a measured or discrete manner. In the illustrated embodiment of FIG. 4, a plurality of recessed detents d1, d2 and d3 are formed on a longitude along an inner radial surface of the piston chamber 82, where each detent is configured to receive and engage with a raised formation, for example, a ridge or, as illustrated, a ball plunger 91 supported and biased by a spring 94 situated in a recess 92, formed on an outer radial surface of the piston 84. Each detent positions the stiffener member 24 within and relative to the catheter shaft 12 such that the distal end of the stiffener member 24 generally sets a location Xi representing a proximal end of the distal deflection section 12D at which its deflection curvature begins. As illustrated in FIGS. 5A, 5B and 5C, locations X1, X2 and X3 enable the distal deflection section 12D to achieve deflection curvatures D1, D2 and D3, respectively. It is understood that the FIGURES, including those illustrating the detents $d_i$ and corresponding locations $X_i$, are not necessarily to scale in relation to each other. It is also understood that the detents may be formed in the outer radial surface of the piston 84, with the raised formation emerging from the inner radial wall of the piston chamber 82.

Optionally, a compression spring 88 may be mounted within the piston chamber 82 to bias movement of the piston relative to the cylindrical body 80 and/or to smooth out this relative movement. The spring 88 may be positioned between the distal end 84D of the distal end 84D of the piston 84 and the distal end of the piston chamber 82. The compression spring 88 can either be arranged between the piston 84 and outer body 80, or can have one end in contact with or fixed to the piston 84, while the other end is in contact with or fixed to the distal end 80D of the outer body 80.

The proximal end of the piston 84 has a threaded outer surface 104. A circular thumb control 106 is rotatably mounted on the threaded outer surface 104 at proximal end of the piston 84. The thumb control 106 has a threaded inner surface 108 that interacts with the threaded outer surface 104 of the piston 84 so that the longitudinal position of the thumb control 106 relative to the proximal end 80P of the outer body 80 is adjustable. The thumb control 106 acts as a stop, limiting the maximum distance that the piston 84 can be pushed distally into the piston chamber 82, and thus the distance that the stiffener member 24 can be extended distally longitudinally relative to the catheter shaft 12. A securing means, such as a tension screw 109 is provided in the thumb control 106 to control the tension between the thumb control and piston 84 for locking and releasing the thumb control in a longitudinal position on the proximal end 84P of the piston. As would be recognized by one skilled in the art, the thumb control 106 can be replaced by any other mechanism that can act as a stop, such as a step on the inner surface 82, for limiting the distance that the piston 84 extends into the piston chamber 82, and it is not necessary, although it is preferred, that the stop be adjustable relative to the piston.

From the deflection curvature adjustment handle 18, the stiffener member 24 extends distally through a protective shaft 96 extending between the distal end of the deflection curvature adjustment handle 18 and proximal end of the deflection rocker handle 16. The stiffener member 24 extends through the deflection rocker handle 16 and into the proximal end of the catheter shaft 12.

Figure 6:
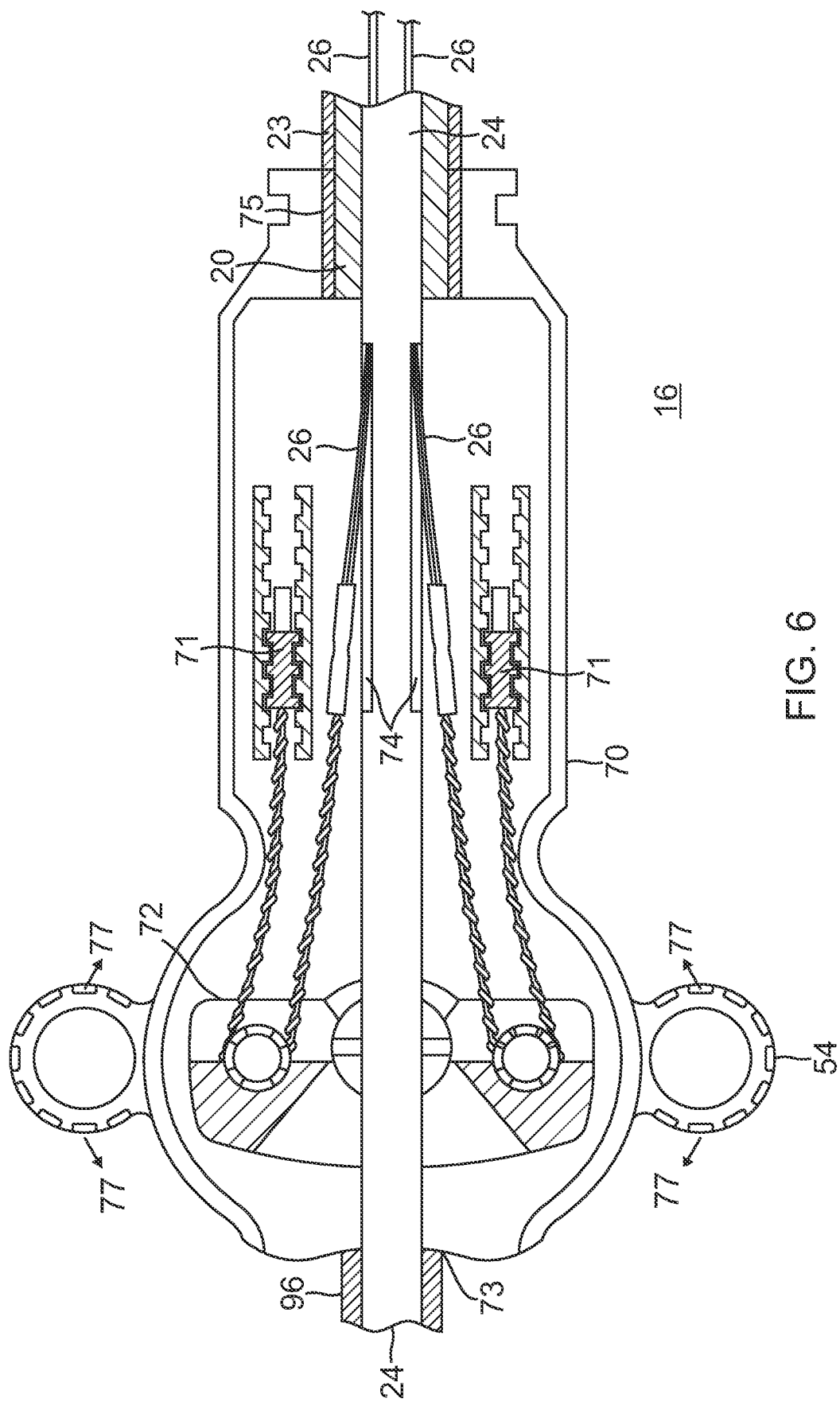
FIG. 6 is a top plan view of a deflection control handle of FIG. 1, with parts broken away.

As shown in FIG. 6, the deflection rocker handle 16 has a housing 70 and pulley assembly 72 around which the puller wires 26 are wrapped to redirect their proximal ends into stops 71 that anchor the proximal ends in the rocker handle 16 at locations distal of the pulley assembly 72. Each of the puller wires 26 may be a subassembly that includes a proximal rope or woven tensile portion that is crimped to the puller wire and wound around the pulley assembly 72. As understood by one of ordinary skill in the art, as an operator pivots or "rocks" the puller assembly 72 in one direction via the rocker arm 54 (sees arrows 77), the puller assembly draws proximally on the one puller wire on that side for deflection in that direction while releasing the other wire distally to facilitate the deflection. The stiffener member 24 extends through the length of the housing 70 between a proximal opening 73 and a distal opening 75, and in between the puller wires 26. In the illustrated embodiment, longitudinal openings or slots 74 are formed in the side wall of the stiffener member 24 so that the puller wires 26 can enter the lumen 25 of the stiffener member 24. The slots 74 have a length sufficient to allow the puller wires 26 to enter the lumen 25 with interfering with the longitudinal movement of the stiffener member 24 relative to the catheter shaft 12. It is understood that the deflection rocker handle 16 and the deflection curvature adjustment handle 18 may be integrated, for example, with the aforementioned piston assembly of the handle 18 may incorporated into the deflection rocker handle 16 distally of the rocker arm 54. Suitable deflection control handles are disclosed in U.S. Pat. Nos. 8,617,087 and 8,747,351, the entire disclosures of which are incorporated herein by reference.

In use, an operator either pulls or pushes piston 84 of the adjustment handle 18 to cause longitudinal movement of the piston relative to the outer body 80 from one detent to another detent, as selected by the operator. This movement causes the stiffener member 24 to move longitudinally within the catheter shaft 12, thereby allowing the operator to vary or adjust the distal end of the stiffener member and thus the type of deflection curvature of the distal deflection section 12D when deflected by the operator via the deflection rocker arm 54 on the control handle 16, as shown in FIGS. 5A, 5B and 5C. By engaging the plunger 91 with a more distal detent, e.g., detent d1, in the adjustment handle 18, as shown in FIG. 4, the piston 84 is set more distally relative to the cylindrical body 80 which positions the distal end of the stiffener member 24 more distally to provide in a smaller or tighter deflection curvature in the distal section 12D. In contrast, by engaging the plunger 91 with a more proximal detent, e.g., detent d3, in the adjustment handle 18, the piston 84 is set more proximally relative to the cylindrical body 80 which positions the distal end of the stiffener member 24 more proximally to provide a larger or looser deflection curvature in the distal section 12D.

In accordance with a feature of the present invention, the catheter 10 is afforded in-plane deflection. As shown in FIGS. 2A and 2B, portions of the multi-layer coil member 20 are fixed or fused, for example, by welding together sections of multiple adjacent coils at 100, in opposite locations along a first diameter 110 to minimize flexion of the coil member 20 within a first plane defined by the first diameter 110 and the longitudinal axis of the coil member 20 while allowing flexion within a second plane generally perpendicular to the first plane. In the illustrated embodiment, the outer layer 20C has portions fused but it is understood that any one or any combinations of the layers 20A, 20B and 20C may have portions fused together and/or fused to each other to accomplish biased or in-plane deflection. In that regard, the puller wires 26 lie along a second diameter 112 generally perpendicular to the first diameter 110. In the embodiment of FIGS. 2A and 2B, the coil member 20 is fixed at its outer coil layer 20C at intermittent welded or fused locations 100 along it length and along the diameter 110 or the X axis, which minimizes flexion of the coil member 20 within X/Z plane while allowing flexion within the Y/Z plane. In that regard, the puller wires 26 lie along the Y axis generally perpendicular to the X axis.

In lieu of or in addition to the fused or welded sections 100, wire members 101 (shown in broken lines in FIG. 2A) may be welded or fused to the coil member along their length to limit or provide reduced flexibility of the coil member in one plane.

In the embodiment of FIG. 2A, the stiffener member 24 is formed with an even distal end 24 to provide symmetrical bidirectional deflection, as shown in FIGS. 5A, 5B and 5C. An even distal end sets a common location Xi along the length of the catheter shaft 12 for initiation of the deflection curvature (or a proximal end of the distal deflection section 12D) regardless of which puller wire is drawn for deflection.

Figure 7:
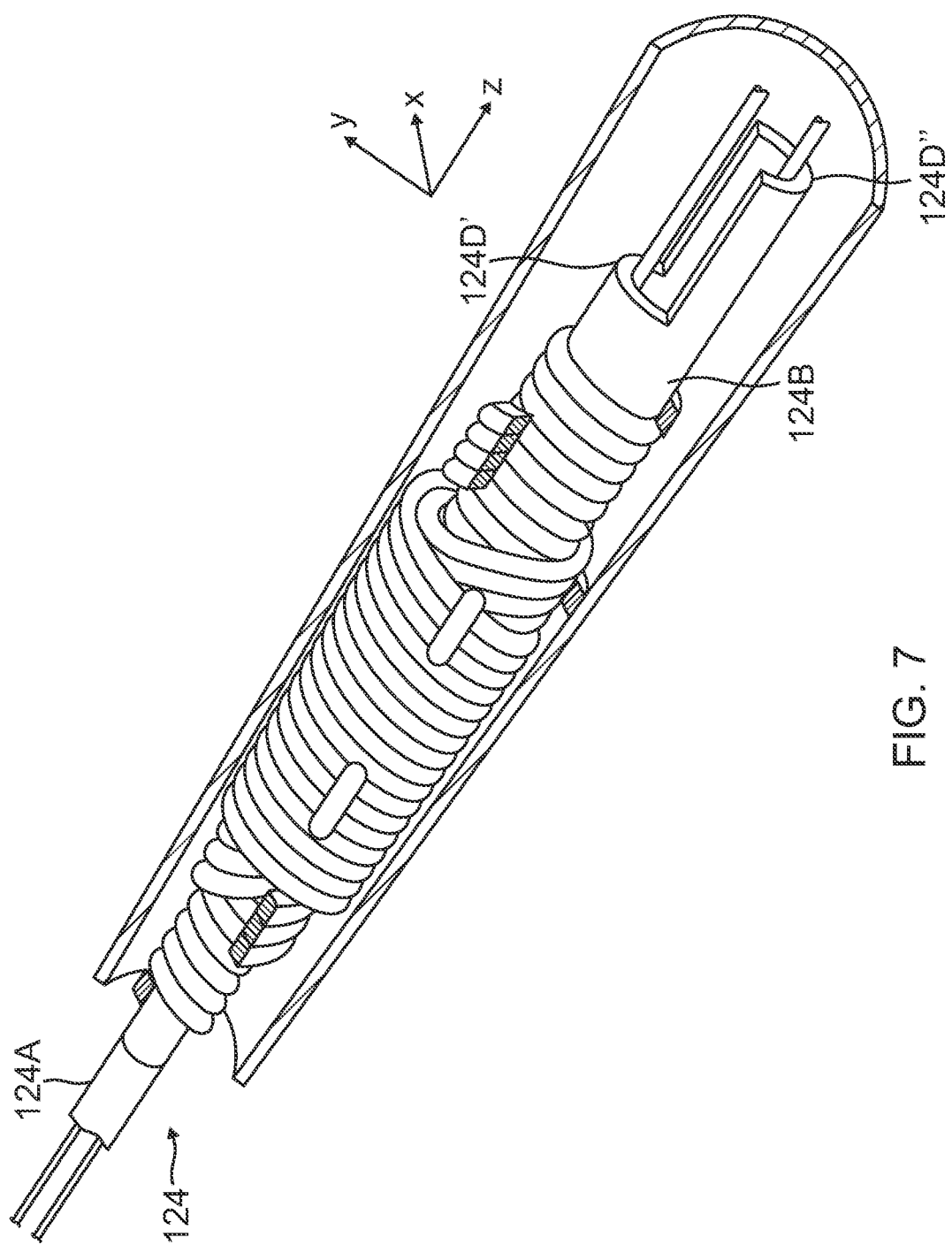
FIG. 7 is a perspective view of a catheter shaft, in accordance with another embodiment of the present invention.
Figure 8A:
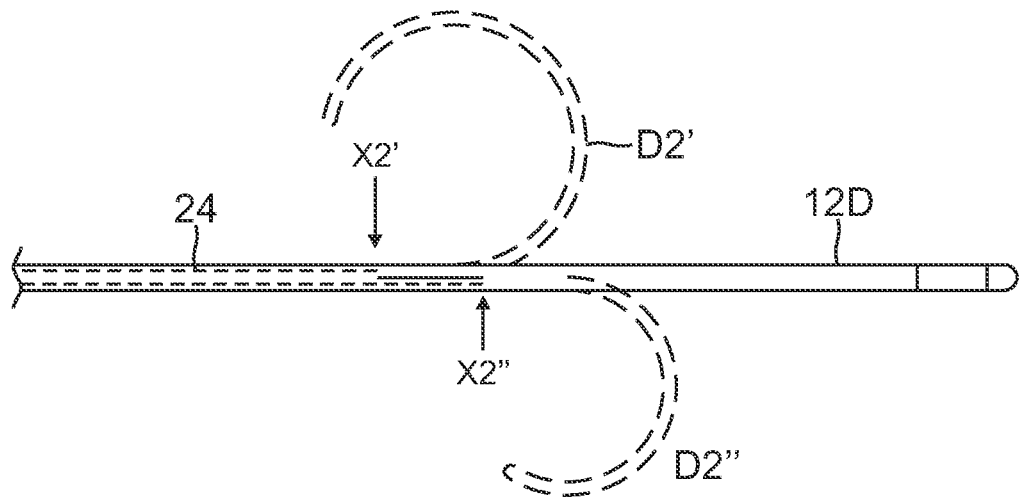
FIGS. 8A, 8B and 8C are schematic representations of asymmetrical bi-directional deflection curvatures of different types or tightness provided by the catheter shaft of FIG. 7.
Figure 8B:
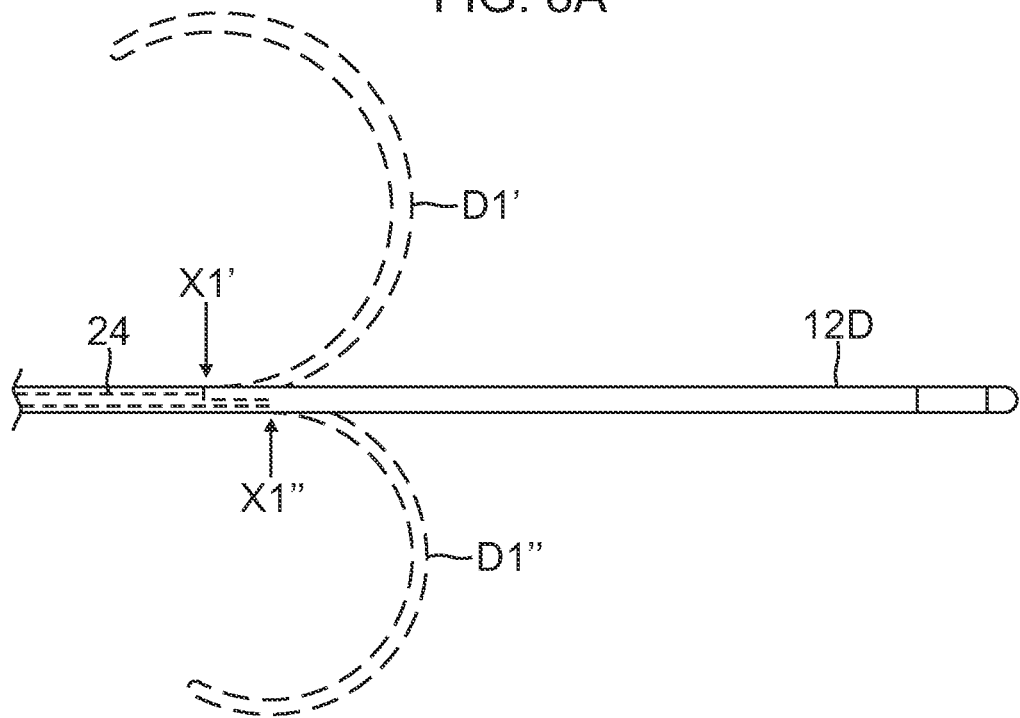
Figure 8C:
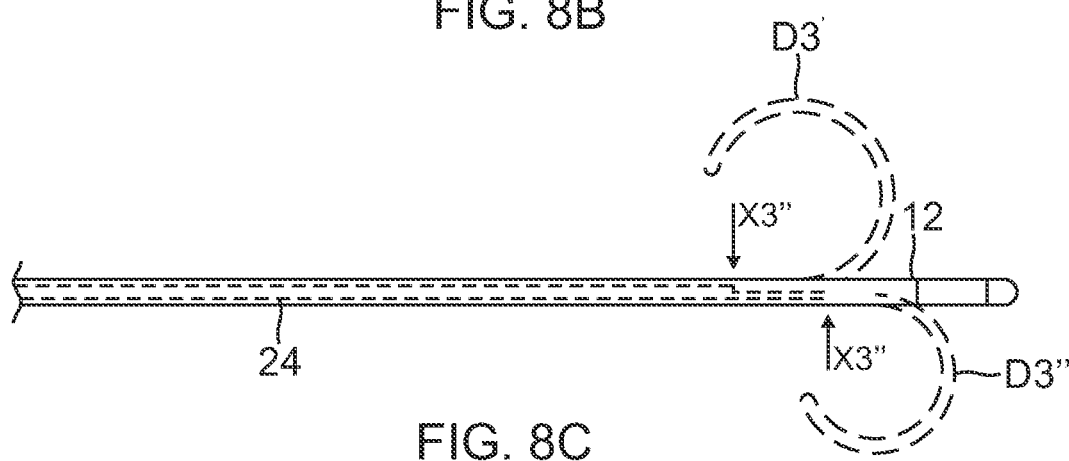

In accordance with a feature of the present invention, stiffener member 124 in accordance with another embodiment as shown in FIG. 7 is formed with uneven (including, e.g., angled, notched or stepped) distal ends 124D' and 124D" to provide asymmetrical bidirectional deflection, as shown in FIGS. 8A, 8B and 8C. For each longitudinal position of the stiffener member 24 relative to the catheter shaft 12, the distal section 12D has a first deflection curvature D1' with a first deflection initiation location X1' (or a first proximal end of the distal deflection section 12D) for one puller wire corresponding with the distal end 124D', and a second deflection curvature D1" with a second deflection initiation location X1" (or a second proximal end of the distal deflection section 12D) for the other puller wire corresponding with the distal end 124D".

To ensure that the portion of the stiffener member 124 extending to the more distal end 24D" has sufficient rigidity to enable deflection on that side of the stiffener member 124, the stiffener member 124 may have a two part construction comprising sections 124A and 124B, wherein the material(s) of which the section 124B is has sufficient rigidity to support the distal end 124D" against excessive flexing or breakage during deflection. For example, the section 124A is constructed of a plastic material and the section 124B is constructed of nitinol, stainless steel, or other suitable metal.

Figure 9:
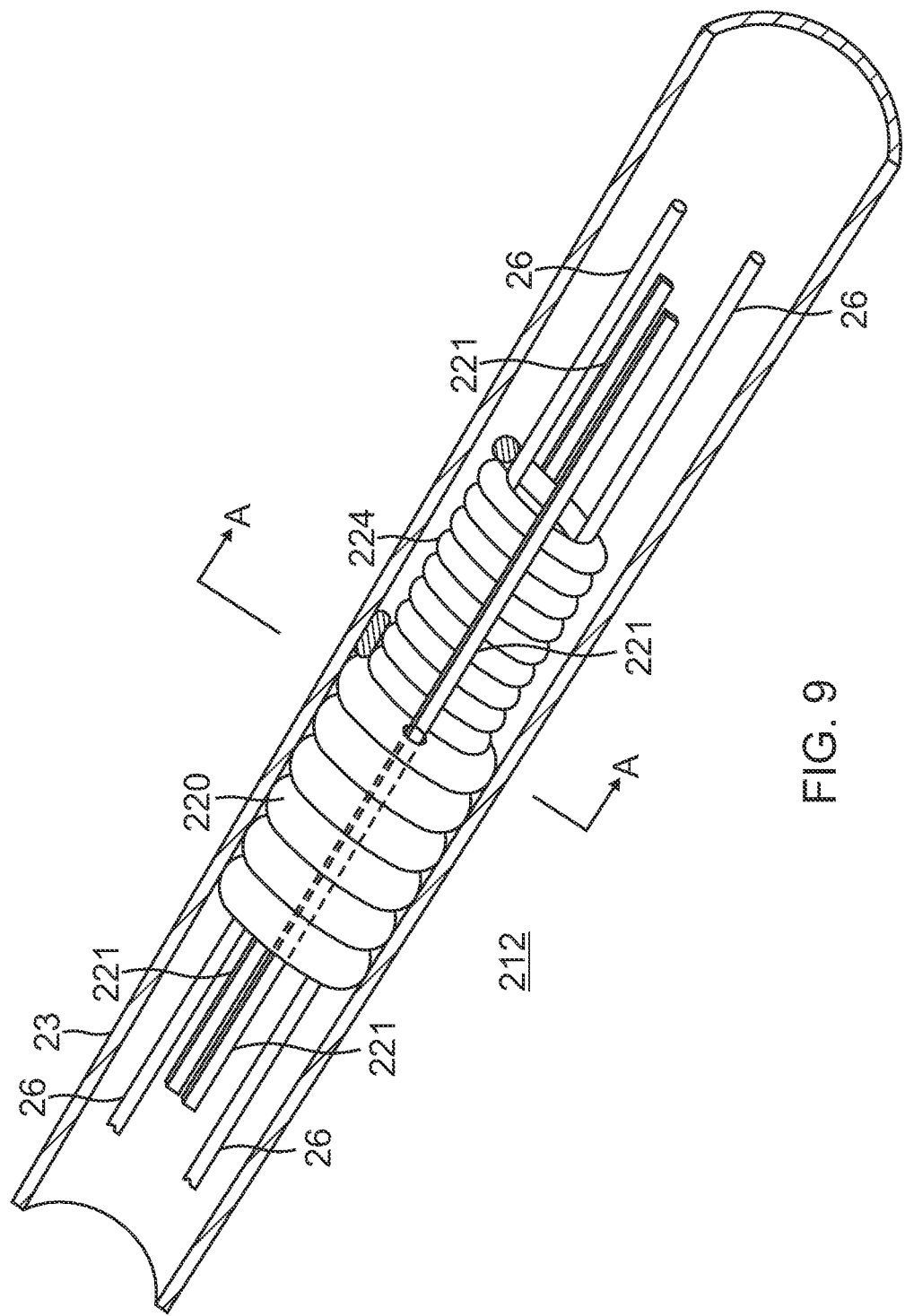
FIG. 9 is a perspective view of a catheter shaft, in accordance with yet another embodiment of the present invention.
Figure 9A:
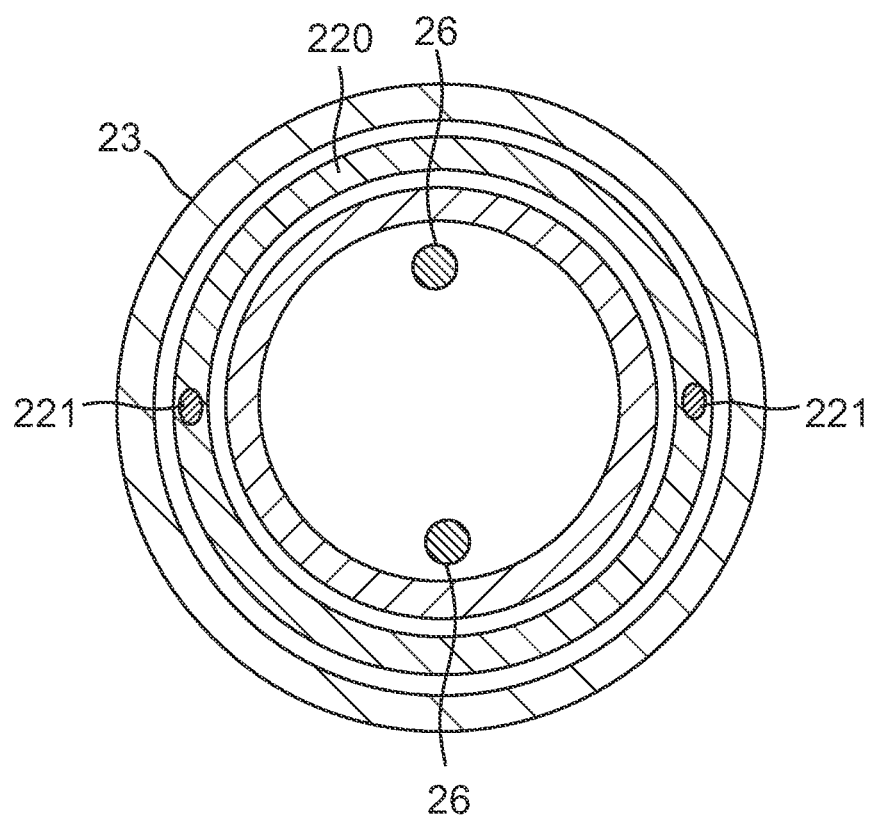
FIG. 9A an end-cross-sectional view of the catheter shaft of FIG. 9, taken along line A-A.

In an alternate embodiment of FIGS. 9 and 9A, a catheter shaft 212 has an outer thin-walled coiled tubular member 220 with a pair of struts 221 embedded or otherwise affixed in opposing locations along a diameter of the tubular member 120. The struts 221 promote bi-directional deflection in a plane generally perpendicular to the diameter. Suitable materials for constructing the struts 221 include, for example, a stiffer polymer or metal wire. Extending through a lumen 122 of the outer coiled tubular member 120, an inner stiffener member 124 has a coiled tubular configuration which minimizes the risk of the stiffener member kinking.

The preceding description has been presented with reference to presently disclosed embodiments of the invention. Workers skilled in the art and technology to which this invention pertains will appreciate that alterations and changes in the described structure may be practiced without meaningfully departing from the principal, spirit and scope of this invention. As understood by one of ordinary skill in the art, the drawings are not necessarily to scale, and any feature or combinations of features described in some embodiments may be incorporated into any other embodiments or combined with any other feature(s) of another embodiment, as desired or needed. Accordingly, the foregoing description should not be read as pertaining only to the precise structures described and illustrated in the accompanying drawings, but rather should be read consistent with and as support to the following claims which are to have their fullest and fair scope.

What is claimed is:

1. A deflection catheter comprising:
(a) a catheter shaft including an outer member having a first center lumen, the outer member being flexible;
(b) an inner stiffener member extending through the first center lumen of the outer member, the inner stiffener member being translatable through the catheter shaft to vary a longitudinal position of the inner stiffener member relative to the catheter shaft, the catheter shaft having a length extending distally beyond the inner stiffener member disposed inside the catheter shaft, the inner stiffener member extending along a longitudinal axis, the inner stiffener member having a second center lumen and an uneven distal end, the uneven distal end including a first distal most surface and a second distal most surface, the second distal most surface being spaced radially from the first distal most surface and separated a distance along the longitudinal axis from the first distal most surface;
(c) a first puller wire extending through the second center lumen of the inner stiffener member and configured to deflect the outer member using the first distal most surface at a first deflection initiation location;
(d) a second puller wire extending through the second center lumen of the inner stiffener member and configured to deflect the outer member using the second distal most surface at a second deflection initiation location, the second deflection initiation location being spaced along the longitudinal axis from the first deflection initiation location; and
(e) a deflection curvature adjustment handle comprising a body with a piston chamber, and a piston coupled to the inner stiffener member to impart longitudinal movement to the inner stiffener member, the piston chamber having a plurality of detents formed on a longitude along an inner radial surface of the piston chamber, the plurality of detents being longitudinally spaced apart from each other at separate longitudinal positions, each detent of the plurality of detents being configured to engage with a plunger disposed on an outer radial surface of the piston depending on a position of the piston in the piston chamber such that the plunger and the plurality of detents cooperate to provide predetermined discrete deflection curvatures.

2. The deflection catheter of claim 1, the first and second distal most surfaces of the inner stiffener member being separated by 180 degrees.

3. The deflection catheter of claim 1, the uneven distal end being sloped.

4. The deflection catheter of claim 1, the uneven distal end being stepped.

5. The deflection catheter of claim 1, the inner stiffener member having a two-part construction, including a more flexible proximal portion and a less flexible distal portion.

6. The deflection catheter of claim 1, the catheter shaft having an elongated proximal section and a distal deflection section, the inner stiffener member being movable along the longitudinal axis relative to the outer member to enable an operator to adjust a location of a proximal end of the distal deflection section along a length of the catheter shaft.

7. The deflection catheter of claim 6, the inner stiffener member defining the proximal end of the distal deflection section.

8. The deflection catheter of claim 1, the inner stiffener member being less flexible than the outer member.

9. The deflection catheter of claim 1, further comprising a compression spring mounted within the piston chamber to bias movement of the piston relative to the body.

10. The deflection catheter of claim 1, the outer member being made from a multi-layered coil, the multi-layered coil including an inner coil and an outer coil.

11. A method of asymmetrically deflecting a deflection catheter, the deflection catheter comprising the catheter according to claim 1, the method comprising:
   (a) actuating the first puller wire to deflect the outer member using the first distal most surface at the first deflection initiation location, the first puller wire passing through a first slot formed through a sidewall of the inner stiffener member; and
   (b) actuating the second puller wire to deflect the outer member using the second distal most surface at the second deflection initiation location, the second puller wire passing through a second slot formed through the sidewall of the inner stiffener member.

12. The method of claim 11, the actuating the first puller wire causing a first deflection curvature, and the actuating the second puller wire causing a second deflection curvature.

13. The method of claim 11, the catheter shaft having an elongated proximal section and a distal deflection section, the method further comprising:
   moving the inner stiffener member along the longitudinal axis relative to the outer member to enable an operator to adjust a location of a proximal end of the distal deflection section along a length of the catheter shaft.

14. The method of claim 11, further comprising translating the inner stiffener member longitudinally relative to the catheter shaft.

15. The deflection catheter of claim 1, the first and second puller wires passing through respective slots formed through a sidewall of the inner stiffener member.

16. A deflection catheter comprising:
   (a) a catheter shaft including an outer member having a first center lumen, the outer member being flexible;
   (b) an inner stiffener member extending through the first center lumen of the outer member, the catheter shaft having a length extending distally beyond the inner stiffener member disposed inside the catheter shaft, the inner stiffener member extending along a longitudinal axis, the inner stiffener member having a second center lumen and an uneven distal end, the uneven distal end including a first distal most surface and a second distal most surface, the second distal most surface being spaced radially from the first distal most surface and separated a distance along the longitudinal axis from the first distal most surface;
   (c) a first puller wire extending through the second center lumen of the inner stiffener member and configured to deflect the outer member using the first distal most surface at a first deflection initiation location;
   (d) a second puller wire extending through the second center lumen of the inner stiffener member and configured to deflect the outer member using the second distal most surface at a second deflection initiation location, the second deflection initiation location being spaced along the longitudinal axis from the first deflection initiation location; and
   (e) a deflection curvature adjustment handle having a body with a piston chamber, and a piston coupled to the inner stiffener member to impart longitudinal movement to the inner stiffener member, the piston chamber having a plurality of detents formed on a longitude along an inner radial surface of the piston chamber, the plurality of detents being longitudinally spaced apart from each other at separate longitudinal positions, each detent of the plurality of detents being configured to engage with a plunger disposed on an outer radial surface of the piston depending on a position of the piston in the piston chamber such that the plunger and the plurality of detents cooperate to provide predetermined discrete deflection curvatures.

17. The deflection catheter of claim 16, further comprising a compression spring mounted within the piston chamber to bias movement of the piston relative to the body.

\* \* \* \* \*